(12) United States Patent
Vogele

(10) Patent No.: US 10,206,708 B2
(45) Date of Patent: Feb. 19, 2019

(54) DEVICE FOR CONTROLLING CORPOREAL STRUCTURES

(76) Inventor: Michael Vogele, Schwabmunchen (DE)

( * ) Notice: Subject to any disclaimer, the term of this patent is extended or adjusted under 35 U.S.C. 154(b) by 1958 days.

(21) Appl. No.: 10/591,821

(22) PCT Filed: Mar. 7, 2005

(86) PCT No.: PCT/EP2005/002386
§ 371 (c)(1),
(2), (4) Date: Jul. 25, 2007

(87) PCT Pub. No.: WO2005/084565
PCT Pub. Date: Sep. 15, 2005

(65) Prior Publication Data
US 2007/0276407 A1    Nov. 29, 2007

(30) Foreign Application Priority Data

Mar. 6, 2004  (DE) .................... 20 2004 003 646 U

(51) Int. Cl.
| | | |
|---|---|---|
| *A61B 17/34* | (2006.01) | |
| *A61B 17/00* | (2006.01) | |
| *A61B 34/00* | (2016.01) | |
| *A61B 90/50* | (2016.01) | |
| *A61B 90/11* | (2016.01) | |

(52) U.S. Cl.
CPC .......... *A61B 17/3403* (2013.01); *A61B 34/70* (2016.02); *A61B 90/11* (2016.02); *A61B 90/50* (2016.02); *A61B 2017/00398* (2013.01); *A61B 2017/3405* (2013.01); *A61B 2017/3409* (2013.01)

(58) Field of Classification Search
CPC ..... A61B 17/3403; A61B 19/26; A61B 19/22; A61B 19/201; A61B 2017/3409; A61B 2017/3405; A61B 2017/00398; A61B 2017/3411; A61B 34/70; A61B 34/72; A61B 34/30; A61B 34/35; A61B 34/37; A61B 2034/301; A61B 2034/302;
(Continued)

(56) References Cited

U.S. PATENT DOCUMENTS 2,982,248 A * 5/1961 Hosko, Jr. .................... 119/729
4,407,625 A * 10/1983 Shum ............................ 414/728
(Continued)

FOREIGN PATENT DOCUMENTS

WO    WO 9720515 A1 * 6/1997 ............. A61B 19/00

*Primary Examiner* — David C Eastwood
*Assistant Examiner* — Tin Nguyen
(74) *Attorney, Agent, or Firm* — Myers Andras LLP; Joseph C. Andras

(57) ABSTRACT

The invention relates to a device for controlling corporeal structures, especially for introducing puncture needles or operation probes. Said device comprises a base plate (1), at least one base holder (2) applied to the base plate (1), and holding rods (3, 4) that are fixed to the base holder in a fixed manner and are used to hold and position a targeting device (10) for a medical instrument (8). The aim of the invention is to create one such device in such a way that it has a simple structure and can guide medical instruments in a variable and precise manner. To this end, the targeting device (10) is mounted on two adjustment arms (7) that can be respectively displaced in the X and/or Y plane, on the free ends of the holding rods (3, 4), by means of an actuating drive (6).

5 Claims, 1 Drawing Sheet

(58) Field of Classification Search
CPC ........ A61B 2034/304; A61B 2034/303; A61B 2034/305; A61B 2034/306
USPC ............ 606/130, 129; 901/15, 16, 14, 8, 28; 600/429; 414/735; 74/490.01–490.15
See application file for complete search history.

(56) References Cited

U.S. PATENT DOCUMENTS

| | | | |
|---|---|---|---|
| 6,406,472 B1* | 6/2002 | Jensen | B25J 9/1065 606/1 |
| 2002/0014017 A1* | 2/2002 | Egan | 33/512 |
| 2002/0128633 A1* | 9/2002 | Brock et al. | 606/1 |
| 2002/0133174 A1* | 9/2002 | Charles et al. | 606/130 |

* cited by examiner

DEVICE FOR CONTROLLING CORPOREAL STRUCTURES

The invention relates to an apparatus for controlling corporeal structures, especially for introducing puncture needles or operation probes.

Such an apparatus is known from the basic concept of WO 97/20515 of the inventor. This targeting device has proven its worth in many surgical or stereotactic operations with precise controlling of points on or in the body. Especially by including state-of-the-art computer technologies such as computer tomography (CT) has it become possible to precisely determine the entrance locations, entrance depths and entrance directions of the medical instruments, so that even a targeting device for guiding these instruments will meet the increased precision. By means of patient data and parameters determined by CT for example, it should be possible to bring an instrument to the defined target point on or in the body.

The relevant aspect in such targeting devices for guiding medical instruments is a high target precision and a rapid reproducibility. The targeting devices still used in practice mostly consist of a massive guide tube which are attached to a stereotactic frame made of metal brackets or bends, e.g. according to U.S. Pat. No. 5,257,998, U.S. Pat. No. 5,176,689 or U.S. Pat. No. 5,201,742. These apparatuses do not fully meet the above requirements because such targeting devices with a heavy stereotactic frame make a reproducible positioning very difficult. The stereotactic precision suffers after repeated surgeries because it is necessary to reset the apparatus for each patient. Since conventional targeting devices are bound to a massive frame, variability is often limited. This also applies to moving towards or accessing the different entrance locations with the targeting device suspended on this frame, especially in the case of a stereotactic operation. The individual body sections of the patient are reconstructed into a 3D object with respective stereotactic spatial coordinates and are transferred to a monitor in the operating theater. This virtual image is calibrated in the operation theater to the patient with the help of a passive mechanical arm which is coupled to the monitor and whose end comprises a probe.

This patient calibration occurs by accessing several points, e.g. anatomically significant points or by X-ray calibration points (marker) on the patient or on the calibration apparatus. Following respective correlation to the reconstructed 3D object on the screen, the computer is enabled to fit this 3D object into this virtual space. The surgeon is able to orient himself during the operation with the help of the reconstructed 3D object and several two-dimensional images which always show the tip of the probe. Even in radiotherapy, puncture needles (so-called pins) are pushed directly into the tumor tissue to be irradiated. Thereafter there is a direct irradiation of the tumor by radioactive substances, starting from the needle tip. It is necessary in this case to push a needle precisely to one point (e.g. the center of the tumor) and to avoid and protect vital structures. Although it has become possible by using computer-supported navigation systems to achieve decisive improvements in this field because the position of the needle tip in or on the body is indicated instead of the position of the probe tip, the demand for a rapid and simple reproducibility still requires improvements in the targeting device in order to enable precise maintaining in all three spatial planes. This is very difficult even for an experienced surgeon due to small inadvertent hand movements. For this reason it is often necessary to withdraw and correct the needle again. Both the high time requirements and the corrections are therefore cumbersome to the patient, since minimal bending of the extremely thin needles may occur. Since bending of the needle cannot be registered or calculated by the computer, the computer supplies erroneous information about the momentary position of the needle tip in space, which may lead to serious consequences.

The invention Is therefore based on the object of providing an apparatus for controlling corporeal structures which meets the above requirements, especially providing a precise, reproducible and variable guidance for medical instruments in combination with a simple structure.

This object is achieved by an apparatus with the features of claim 1.

Any desirable spatial positioning and precise alignment of the targeting device is possible by attaching two actuating drives which are preferably arranged directly above one another and each comprise an adjustment arm which is movable in an X-Y plane. The actuating drives can be triggered or remote-controlled separately or alternatingly in their X- and/or Y-axes, so that the targeting device can be adjusted exactly and rapidly by said actuating drives in order to enable a purposeful setting of the targeting device in the spatial axes. This enables taking a very precise bearing of previously determined (e.g. by CT) surgical or target locations from rooms adjacent to the operating theater, so that a substantial reduction in the radiation exposure of the operating staff is achieved, as is a facilitation in the operations usually conducted in neurosurgery by the precise guidance of instruments, especially puncture needles or surgical probes.

Preferred embodiments are the subject matter of subclaims. Especially appropriate is the arrangement of actuating drives as stacked flat boxes and the configuration of the adjustment arms which are bent towards the patient. In this way the desired spatial points in the system coordinates can be accessed as in the imaging methods as reference planes. The targeting device especially comprises a guide tube with ball heads at the end sides in order to support the instruments as far as possible. This targeting device thus allows the introduction of the instruments in a precise positional setting with respect to each other. Once the holder has been manually preset to the center of the tumor for example, the fine positioning of the instruments can occur by the remote-controlled actuating drives from another room in order to advantageously reduce the radiation exposure of the staff in radiation therapy. Once the targeting device has been pre-adjusted, it is also possible to perform a simulation, such that the needle or probe tip is guided around in the area of the stereotactic space by means of the actuating drives for example, with the position in or on the virtual patient being monitored on the monitor.

A preferred embodiment is described by reference to the drawings, wherein.

Figure 1:
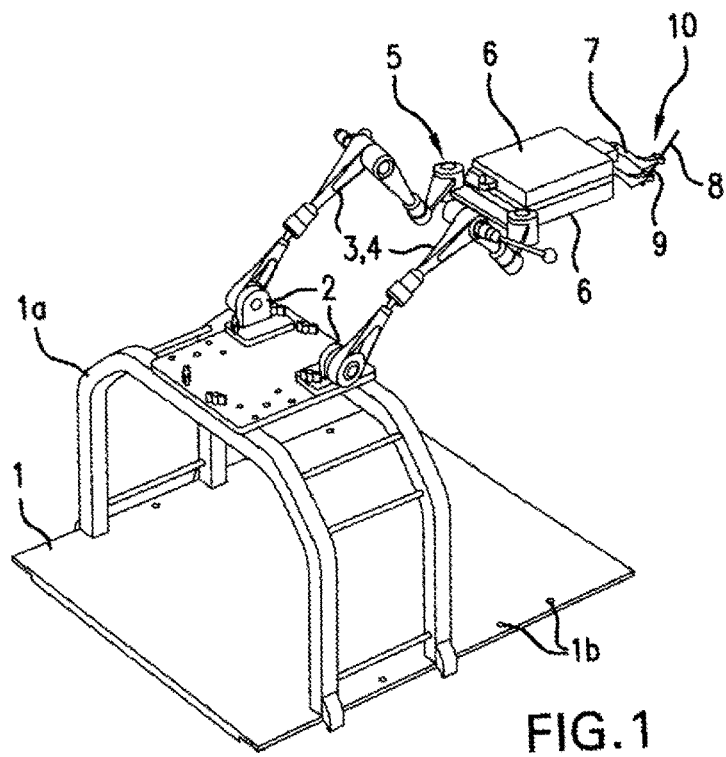
FIG. 1 shows a perspective view of an apparatus with a base plate, two base holders with base and holding rods which are connected with ball joints.

For fixing a targeting device 10, a base plate 1 which is made of stainless magnetizable steel is connected on its bottom side with an operating table, e.g. with metal claws which are screwed together with the base plate 1. The base plate 1 can be adjusted relative to the operating table in the horizontal and vertical direction, with a high strength being ensured. The parts of the holder carrying the target device 10 each consist of a base holder 2 and holding rods 3 and 4 which are linked to the same and which each comprise at the free end a bearing 5 for fastening the actuating drives 6 for the targeting device 10. The base holder 2 can be anchored at any position of the base plate 1 in a mechanical, magnetic or pneumatic way. A scaffold-like frame 1a is provided for this purpose which covers the patient. The linked connection of the holding rods 3 and 4 can each be fixed by means of arresting devices, which in this case are tommy bars as shown here, so that the power transmission and thus the positional fixing of the actuating drives 6 is ensured with their adjustment arms 7 which are movable in the X-Y plane.

A guide tube 9 for a medical instrument 8 for accessing a target tissue Z is held on the ball heads 9a at the free ends of the two bent adjustment arms 7. A probe or an insert tube for adjustment to the used instrument 8 can be introduced into the guide tube 9, especially a puncture needle 8 provided with a stop for axial setting, as is shown here. The axial position of the instrument 8 can also be precisely fixed by a clamping device. For the purpose of preliminary adjustment of the targeting device 10, the two base holders 2 or the frame 1a are pre-positioned on the base plate 1 by means of markings 1b, Thereafter, a probe for example is inserted into the guide means 9 and then the probe is guided in the virtual space for such a time until the probe tip is approximately situated at the desired entrance point and the projection line (=extension of the probe tip along the probe axis) is congruent with the forward feed direction (which can be seen on the monitor).

The staff can then leave the radiation room and the desired target point Z can be approached precisely by remote-controlling the actuating drives 6. The entrance point and the entrance direction of the targeting device 10 are finely adjusted in this process by fine adjustment of the adjustment arms 7 in the X-Y plane. The entire targeting device 10 in relation to the stereotactic frame 1a and thus to the calibration apparatus and to the patient can be set precisely in advance by a simulation (without the patient). During surgery, the patient is then fitted in precisely the same manner into the frame 1a as he was scanned in the CT. The navigation system is now calibrated and the targeting device 10 is attached in a stereotactic correct manner. For checking purposes a probe can be introduced again into the already adjusted targeting device 10. If necessary, the probe can be readjusted. The readjustment can be performed rapidly if necessary, because the probe already nearly has the correct position by the pre-adjustment and the instrument can be readjusted rapidly and precisely to the target location Z by the actuating drives 6.

Figure 2:
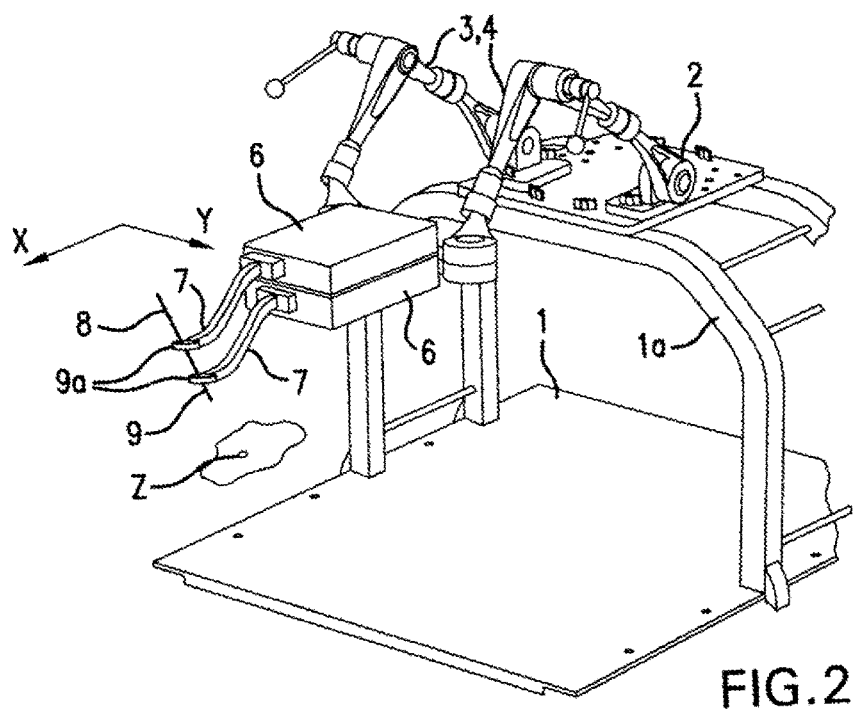
FIG. 2 shows a perspective view in the opposite direction as in FIG. 1 with a slightly enlarged representation of the targeting device.

After reaching the target point Z with the needle tip, the actual irradiation of the tumor can commence. After a one-off simulation and pre-adjustment of the probe, the operation can be performed on the patient any desired number of times. The bearing of the targeting device 10 with the guide tube 10 on the two adjustment arms 7 of the superimposed actuating drives 6 is of relevant importance here. These actuating drives 6 with an X-drive element and Y-drive element each (preferably threaded spindles) in the form of a compound slide are arranged directly above one another (also see FIG. 2). The actuating drives 6 can thus displace the adjustment arms 7 in the longitudinal and/or transversal direction, so that the guide tube 9 is arranged to be swivelable into any angular position and is also arranged in a displaceable way in order to displace the targeting device 10 by the actuating drives in the X- and/or Y-direction and to also turn the same about its rotational axes. FIG. 2 shows the targeting device 10 swiveled in an inclined position upwardly to the left. The instrument 8 which is inserted into the guide tube 9 is also swiveled, so that another target can be accessed from the originally planned target Z. For this purpose, the lower actuating drive 6 could be displaced transversally to the left in order to position the guide tube in a steeper way and to thus achieve a fine adjustment of the target direction precise to the millimeter of a relatively thin puncture needle.

The right part of FIG. 2 shows the fixing of the actuating drives 6 in closer detail. They are connected via the holding rods 3 and 4 with ball joints to the base holders 2. The ball joints can be arrested, such that a locking device is actuated by means of a tommy bar. Notice must be taken that by arranging the targeting device 10 on the two actuating drives 6 the spatial position of the guide tube 9 for guiding the instrument 8 can be set at will, with a fine adjustment being enabled by the actuating drives 6. An adjustment of the targeting device 10 in any desired spatial manner is thus enabled. By lowering the holding rods 3 and 4, the targeting device 10 can be lowered towards the patient in order to be brought as close as possible to the target location Z and to prevent bending of the thin needles.

The invention claimed is:

1. An apparatus for controlling a targeting device for precisely positioning a medical instrument in preparation for introducing the medical instrument into a patient at a desired entrance point and at a desired entrance angle, comprising:
   a scaffold-like frame that is configured for surrounding the patient;
   first and second base holders repositionably attached in a spaced apart manner to the scaffold-like frame;
   first and second holding rods with proximal ends attached to the first and second base holders in an articulated manner;
   first and second ball joint bearings attached to a distal end, respectively, of a corresponding one of the first and second holding rods;
   first and second actuating drives attached to a corresponding one of the first and second ball joint bearings, the first and second actuating drives arranged substantially above one another, the first and second actuating drives repositionable relative to one another;
   first and second fine-position adjustment arms extending from the first and second actuating drives, respectively, each of the first and second fine-position adjustment arms independently movable in an X- and/or Y-plane by the corresponding actuating drive, and
   a guide tube for the medical instrument, the guide tube having a tip, a first portion of the guide tube pivotally mounted to a free end of the first fine-position adjustment arm and a second portion of the guide tube pivotally mounted to a free end of the second fine-position adjustment arm such that repositioning of the first and second actuating drives, movement of the first and second fine-position adjustment arms, or both, interoperate to move the tip of the guide tube and vary an angle of the guide tube; wherein
   the first and second holding rods are articulated relative to the scaffold-like frame via the first and second base holders for a coarse preliminary positioning and holding of the tip of the guide tube near the desired entrance point and near the desired entrance angle;
   the first and second actuating drives are pre-positioned with the first and second ball joint bearings relative to one another for an intermediate positioning and holding of the tip of the guide tube near the desired entrance point and near the desired entrance angle; and the first and second fine-position adjustment arms are moved in the X- and/or Y-plane by the first and second actuating drives, respectively, for a fine sub-millimeter positioning and holding of the tip of the guide tube at the desired entrance point and at the desired entrance angle.

2. The apparatus according to claim 1, wherein the first and second fine-position adjustment arms are bent away from the first and second actuating drives and towards the patient.

3. The apparatus according to claim 1, wherein the guide tube for the medical instrument is mounted on the free ends of the fine-position adjustment arms, by way of ball heads.

4. The apparatus according to claim 1, further comprising a base plate for supporting the scaffold-like frame, the scaffold-like frame fastened to the base plate in a magnetic, pneumatic or mechanical manner, and wherein the base plate comprises markings for repositioning the scaffold-like frame relative to the base plate.

5. The apparatus according to claim 1, wherein the actuating drives each comprise a compound slide for independently adjusting the respective fine-position adjustment arm in the X-Y plane with remote-controllable threaded spindles.

\* \* \* \* \*